United States Patent
McKearin (12)

(10) Patent No.: US 6,646,157 B2
(45) Date of Patent: Nov. 11, 2003

(54) METHOD FOR MAKING HBED

(75) Inventor: James M. McKearin, Litchfield, NH (US)

(73) Assignee: Geltex Pharmaceuticals, Inc., Waltham, MA (US)

(*) Notice: Subject to any disclaimer, the term of this patent is extended or adjusted under 35 U.S.C. 154(b) by 480 days.

(21) Appl. No.: 09/748,306

(22) Filed: Dec. 21, 2000

(65) Prior Publication Data

US 2001/0047108 A1 Nov. 29, 2001

Related U.S. Application Data

(60) Provisional application No. 60/171,673, filed on Dec. 21, 1999.

(51) Int. Cl.[7] .................. C07C 229/00; C07C 61/00
(52) U.S. Cl. .................. 562/443; 562/433; 562/400
(58) Field of Search .................. 562/443, 433, 562/400

(56) References Cited

U.S. PATENT DOCUMENTS

| | | |
|---|---|---|
| 3,005,848 A | 10/1961 | Knell et al. |
| 3,758,540 A | 9/1973 | Martell |
| 3,833,590 A | 9/1974 | Dazzi |
| 4,044,036 A | 8/1977 | Hari et al. |
| 4,116,991 A | 9/1978 | Leneuf |
| 4,129,556 A | 12/1978 | Zondler et al. |
| 4,130,582 A | 12/1978 | Petree et al. |
| 4,352,751 A | 10/1982 | Wieder et al. |
| 4,454,106 A | 6/1984 | Gansow et al. |
| 4,528,196 A | 7/1985 | Pitt |
| 4,647,447 A | 3/1987 | Gries et al. |
| 4,909,257 A | 3/1990 | Engelstad et al. |
| 5,057,302 A | 10/1991 | Johnson et al. |
| 5,227,474 A | 7/1993 | Johnson et al. |
| 5,376,154 A | 12/1994 | Daly et al. |
| 5,534,241 A | 7/1996 | Torchilin et al. |
| 5,539,138 A | 7/1996 | Flanagan et al. |

FOREIGN PATENT DOCUMENTS

| | | |
|---|---|---|
| EP | 0367223 A2 | 10/1989 |
| WO | WO 95/16663 A1 | 6/1995 |
| WO | WO 97/36885 A1 | 10/1997 |
| WO | WO 97/44313 A1 | 11/1997 |
| WO | WO 97/44313 * | 11/1997 |
| WO | WO 99/39706 A1 | 8/1999 |

OTHER PUBLICATIONS

Martell et al., "Synthesis of N,N'–di(2–hydroxybenzyl)ethylenediamine–N,N'–diacetic acid (HBED) and derivatives," *Canadian Journal of Chemistry*, vol. 64, No. 3, pp. 449–456, Mar. 1986.

Bergeron et al., "HBED: A Potential Alternative to Deferoxamine for Iron–Chelating Therapy," *Blood*, 1998, pp. 1445–1452, vol. 91, No. 4.

Grady, R. W., et al., Title of Relevant Chapter: "Preliminary Results From a Phase I Clinical Trial of HBED," *Development of Iron Chelators for Clinical Use*, 1994, Chapter 18, pp. 395–406.

Database Caplus on STN, Department of Medicinal Chemistry, (FL, USA), Accession No. 1998:105731, HBED: A potential alternative to deferoxamine for iron–chelating therapy. Blood. 1998, vol. 91, No. 4, pp. 1446–1452.

Database Caplus on STN, Medical College (NY, USA), Accession No. 1996:205010, Grady et al., Preliminary results from a phase I clinical trial of HBED. Dev. Iron Chelators Clin. Use. 1994, pp. 395–406.

* cited by examiner

*Primary Examiner*—Alan L. Rotman
*Assistant Examiner*—Hector M. Reyes
(74) *Attorney, Agent, or Firm*—Cooley Godward LLP

(57) ABSTRACT

The preparation of a mono-cationic salt of N,N'-bis(2-hydroxybenzyl)-ethylenediamine-N,N'-diacetic acid (HBED) and HBED itself is disclosed. In particular, the invention relates to the hydrolysis of the t-butyl ester of HBED with a weak acid, such as formic acid, to form HBED, and the subsequent reaction with an equimolar amount of a base to form the mono-cationic salt.

4 Claims, No Drawings

METHOD FOR MAKING HBED

This application claims the benefit of Provisional Application No. 60/171,673, filed Dec. 21, 1999.

TECHNICAL FIELD

This invention relates to a method for making N,N'-bis(2-hydroxybenzyl)-ethylenediamine-N,N'-diacetic acid (HBED). The invention also relates to a method for making the cationic salts of HBED, particularly the mono-cationic salt such as the mono-sodium salt.

BACKGROUND

Until the discovery of the mono-sodium salt of HBED and its unique properties as a subcutaneously or intravenously injectable solution (see for example PCT International Application No. PCT/US 99/02388 filed Feb. 3, 1999), a commercially useful method for making the compound, per se, was not known. While the PCT Application discloses the compound and a method for making it, there has been no direct route to make HBED or its cationic salts, e.g. the mono-sodium salt. Generally, HBED is available commercially as the mono hydrochloride salt or the dihydrochloride salt. Thus, in order to form the mono-cationic salt, the mono- or di-acid had to be neutralized and then carefully titrated to form the mono-cationic salt. When the desired active material was the mono-cationic salt, it would have to be extracted from the significant amount of sodium chloride that was formed from the dihydrochloride. The process of the invention described herein avoids the salt formation and provides a way to make HBED neat, which can then be converted to a cationic salt using a base such as sodium hydroxide.

SUMMARY OF THE INVENTION

One aspect of the invention is a process of forming N,N'-bis(2-hydroxybenzyl)-ethylenediamine-N,N'-diacetic acid (HBED), which process comprises hydrolyzing a compound of Formula (3) as shown in the reaction sequence I, preferably, using a weak acid in an aqueous environment. Preferably, the compound of Formula (3) is formed by reacting a compound of Formula (2) with at least two molar equivalents of the t-butyl ester of a 2-haloacetic acid. The compound of Formula (2) is shown in reaction sequence I as well.

Another aspect of the invention is the process wherein the compound of Formula (2) is prepared by reducing the compound of Formula (1) which is represented in the reaction sequence as well.

Another aspect of the invention is a process for forming the mono-cationic salt of HBED by reacting one molar equivalent of an organic or inorganic base with HBED itself.

DETAILED DESCRIPTION AND PRESENTLY PREFERRED EMBODIMENTS

This invention is a method for making HBED and its mono- or di-cationic salts. These are referred to as "cationic" salts with reference to the presence of a cation (positive) entity shown as "M" in formula (5). The essence of the process is the hydrolysis of the diester of HBED to form HBED itself. By reacting HBED itself with the appropriate molar quantity of a base such as sodium hydroxide the corresponding cationic salt (preferably the mono-cationic salt) is formed. The overall sequence, which starts from readily available starting materials can be seen in reaction sequence I.

Reaction sequence I is as follows.

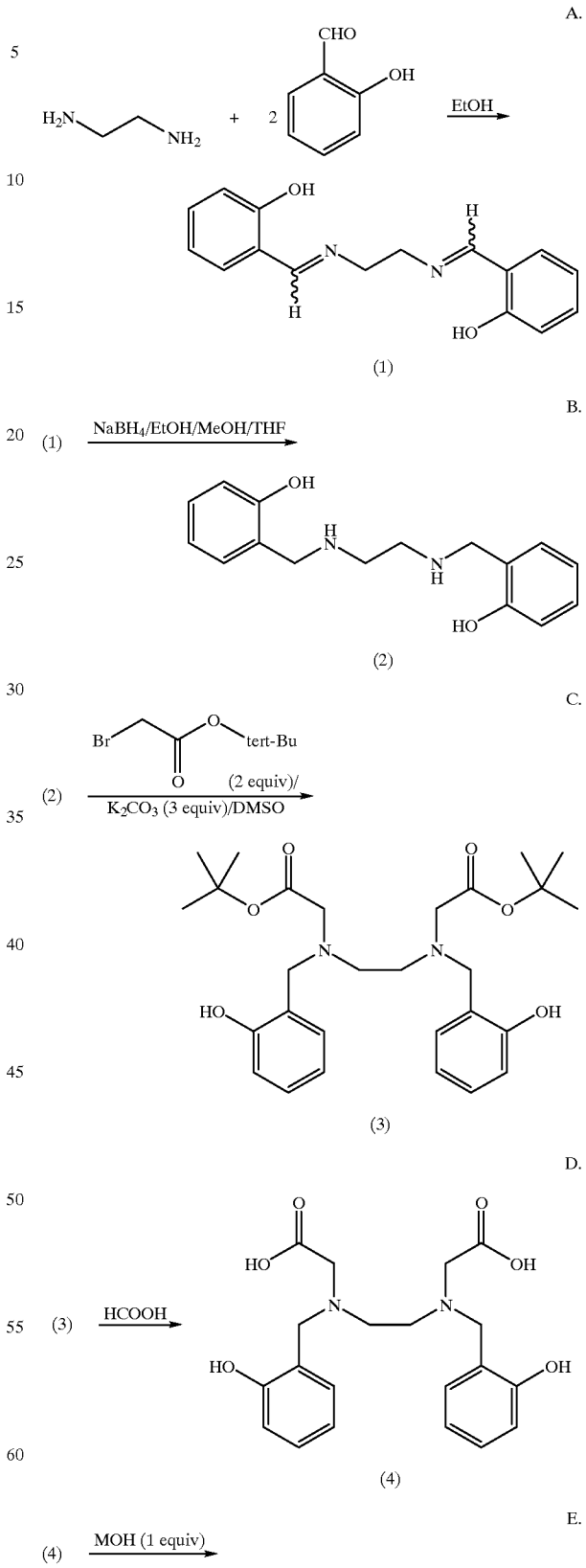

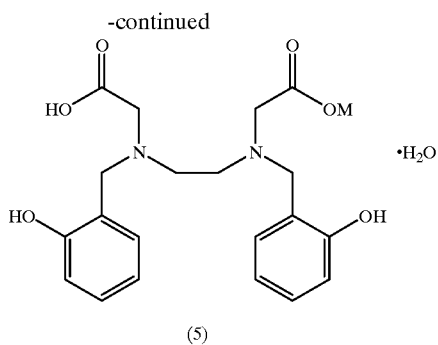

(5)

In reaction sequence I and throughout the specification, certain abbreviations are used as follows:

C=centigrade
DCM=dichloromethane (methylene chloride)
DMSO=dimethyl sulfoxide
EtOH=ethanol
gal=gallon
IPA=isopropanol
Kg=kilogram
L=liter
MeOH=methanol
mg=milligram
ml=milliliters
MOH=akaline hydroxide ($M^+$=monocation)
$NaBH_4$=sodium borohydride
THF=tetrahydrofuran
TLC=thin layer chromatography In the first Step A, ethylenediamine (available from Sigma, P.O. Box 14508, St. Louis, Mo. 63178) is reacted with 2 molar equivalents of o-hydroxybenzaldehyde (also available from Sigma as salicylaldehyde) in a suitable solvent such as an alkanol, particularly ethanol or EtOH/5% IPA, to form the compound of Formula (1). Generally this is carried out at a temperature of about 0° C. to about 20° C. with cooling, as the reaction is exothermic. Generally the pressure will be about atmospheric with the reaction taking place under an atmosphere of a non-reactive gas such as nitrogen. The reaction time will generally be about 5 to about 24 hours, at least about 16 hours.

In the second Step B, the compound of Formula (1) is reacted with a reducing agent to hydrogenate the double bonds to form the compound of Formula (2). Generally, this is done with sodium borohydride in a suitable solvent or solvent mixture. A suitable solvent is, e.g., a mixture of ethanol (e.g. denatured), methanol, and tetrahydrofuran (THF). Alternatively, a mixture of THF and EtOH/5% IPA may be used. The solvent is present in a quantity sufficient to dissolve compound (1) and the sodium borohydride. The ratio of THF to the other component will be about 2:1 to about 5:1. This step is carried out at a temperature of about 0° C. to about 50° C., preferably less than 30° C. Generally the pressure will be about atmospheric with the reaction taking place under an atmosphere of a non-reactive gas such as nitrogen. The reaction time will generally be about 10 to about 20 hours.

In Step C, once the compound of Formula (2) is prepared, it is reacted with at least 2 molar equivalents, e.g. 2.1, of tertiary butyl ester of a haloacetic acid, e.g. bromoacetic acid. This is done in the presence of a weak base such as potassium carbonate and an organic solvent such as DMSO. It may be useful to include t-butyl ammonium bromide. This results in the tertiary butyl ester of HBED that is shown as Formula (3) in reaction sequence I. This step is carried out at a temperature of about 10° C. to about 50° C. and atmospheric pressure. Other useful solvents include, e.g., chloroform. The reaction time will generally be about 10 to about 100 hours, preferably about 40 to 48 hours.

In Step D, the resulting ester is then hydrolyzed with a weak acid, such as formic acid, in a non-aqueous environment to give the compound identified as Formula (4), which is HBED itself. This step is carried out at a temperature of about 20° C. to about 65° C. and atmospheric pressure. The reaction time will generally be about 10 to about 100 hours, generally less than 50.

In Step E, HBED is then reacted with one molar equivalent of an organic or inorganic base to give the cationic salt, e.g. the monocationic salt shown as Formula (5) in Step E. The pharmaceutically acceptable monocationic salts prepared in accordance with the process of this invention are preparable from an inorganic or organic base. The salt derived from inorganic bases include, but are not limited to, the cations sodium, potassium, lithium, and ammonium. These are readily obtained from the corresponding hydroxides. Salts derived from organic bases include, but are not limited to, salts of primary, secondary, and tertiary amines; substituted amines including naturally-occurring substituted amines and cyclic amines. These include methylamine, ethylamine, isoproplylamine, trimethylamine, triethylamine, tripropylamine, ethanolamine, 2-dimethylaminoethanol, tromethamine, lysine, arginine, histidine, caffeine, procaine, hydrabamine, choline, N-alkylglucamines, theobromine, purine and the like. The mono-sodium salt and the mono-ammonium salt are the two compounds that are particularly preferred. This step is carried out at a temperature of about 2° C. to about 50° C. (preferably about 40–45° C.) and atmospheric pressure. The reaction time will generally be about 1 to about 5 hours, e.g. about 1.5 to 2.5 hours.

As pointed out in PCT Application No. PCT/US99/02388, the HBED mono-cationic salts are particularly useful for treating iron overload by subcutaneous injection.

EXAMPLE I

This example explains how to make a mono-cationic salt of HBED. The formula numbers (1)–(5) may be found in the Detailed Description section of the specification.

A. Monosodium HBED (1) Ethylene diamine (MW=60.1, d=0.899) (475 g, 528 ml, 7.91 moles) was added at a rapid dropwise rate from a constant pressure addition funnel to a solution of salicylaldehyde (MW=122.12, d=1.146)(1.93 Kg, 1.68 liters (L), 15.8 moles, 2.0 equiv.) in ethanol over 1.15 hours. The exothermic reaction was kept below reflux using a water bath periodically. During the addition, another 300 ml of EtOH was added to facilitate stirring which was continued overnight. The reaction mixture was cooled for 1 hour in an ice bath and filtered to give yellow iridescent flakes and a brown solution. The solid product was washed with EtOH (1.2 L) and air dried to produce 2314 g of a compound of formula (1) (109% yield) (MW=268.32).

(2) $NaBH_4$, (628 g, 16.6 moles, 2.1 equiv was added to a stirring solution of the compound of formula (1) (2122 g, 7.91 moles) in 7 L of EtOH and 17 L of THF in 50 g portions. The addition required 6 hours. The reaction was allowed to react overnight. It was concentrated in vacuo to remove the solvents, the residue was dissolved in DCM (17 L), washed with water (3 L) and dried over $Na_2SO_4$ then filtered. Concentration in vacuo to approx. 4 L gave a heterogeneous mixture which was filtered and the resulting solid was washed with 1:1 DCM:Hexane. It was washed with another 2 L of hot DCM. Hexane (2 L) was added to the DCM and a precipitate formed. Hexane (6 L) was added to the DCM filtrate (6 L) and a precipitate formed. The DCM/Hexane mixtures were filtered and the resulting solid dried to give 876 g (41%, 3.22 moles) of a white solid identified as formula, (2), TLC(9:1:0.3 DCM:MeOH:NEt$_3$) showed one spotmp 122–135° C.

(3) Potassium carbonate (691 g, 5.0 moles, 3.0 equiv.) was added to a stirred solution of the compound of formula (2) (450 g, 1.64 moles) in DMSO (1.91). This was cooled to 12°–14° C. using a water bath, and t-butyl bromoacetate (683 g, 3.50 moles, 2.1 equiv.) was added over 30 minutes. After 2 days at room temperature, the reaction was poured into DCM (1.5 L). This was filtered and washed with water (7×1.5 L), dried (NaSO$_4$) and filtered. The DCM was removed in vacuo to give a white foam. This was dissolved in warm (45° C.) benzene (375 ml). The solution was added to well stirred hexane (2.5 L), after 15–20 minutes, a precipitate formed. The solution was cooled in an ice bath for 2 hours the product filtered, washed with hexane, air dried and then dried in vacuo under high vacuum at 30°–35° C. to give 450 g of a white solid identified as formula (3) (0.9 moles, 54%) mp=80°–81° C.

(4) Cold formic acid (1 L) was added to the compound of formula (3) (450 g, 0.9 moles) and stirred at room temperature for 5 days. This was poured into diethyl ether (4 L) while swirling to give 2 layers. The top layer was decanted and discarded. The heavy layer was poured into stirred diethyl ether (3 L), giving a white solid. The liquid phase was decanted and the resulting solid dissolved in EtOH (absolute, 1.5 L, no heat). This was poured into stirred diethyl ether (2.5 L) to again give a white solid and clear solution. The solid was dissolved in EtOH (absolute, 1.6 L, no heat) and stirred overnight. The solution was poured into stirred diethyl ether (3.5 L). The resulting solid was filtered, washed with ether, then quickly transferred to a flask and toluene (0.5 L) added. This was removed in vacuo at 25° C. The white solid was dried overnight in a vacuum oven at 25° C. to give 145 g of a white solid. This solid was treated with acetonitrile (1.4 L) while being stirred, then water (140 ml) added. The resulting heterogeneous mixture was stirred for 1 hour, and then filtered, the solid was washed with acetonitrile then DCM, giving 105 g of HBED after drying at 25° C. under high vacuum overnight. 94 g of this was treated with EtOH (absolute, 450 ml) and stirred for 4 hours. It was filtered, washed with more EtOH (150 ml) and then dried overnight under high vacuum at 25 C, giving 89.6 g, 0.23 moles, 26% yield of HBED, shown as formula (4).

(5) HBED (89 gms, 0.23 moles) was placed into a 1 L Ehrlenmeyer flask with a magnetic stir bar and water (JT Baker, cat #4218-03,100 ml) added. This heterogenous solution was stirred and cooled in an ice bath for 10 minutes then a solution of aqueous sodium hydroxide (13.29 g, 0.23 moles (prepared from Alfa Aesar cat #41281 and JT Baker water, 340 ml)) was added dropwise over 30 minutes to provide a mixture having a pH=7.2. A precipitate began to form, which redissolved upon addition of more water (100 ml). The solution was filtered through 0.45 micron filters (Whatman, PTFE), Concentrated in vacuo at 25°–30° C. and further drying under high vacuum at room temperature for 2.5 days gave 91 g of a white solid, confirmed to be HBED, monosodium salt, the compound of formula (5) where M is Na.

B. Other Monocationic Salts of HBED.

By following the procedure of part A of this example but substituting other bases for NaOH in step (5), other salts are obtained, such as:
monoammonium HBED,
monopotassium HBED,
monolithium HBED, and the like.

EXAMPLE II

This example provides modified method for making the mono-sodium salt of HBED. The compounds represented by formulae numbers (1)–(5) may be found in Reaction Sequence I of this specification.

1. One hundred twenty L of a mixture of EtOH with 5% IPA is charged to a 50 gal reactor. The reactor is purged with nitrogen and a nitrogen bleed is established for the rest of step 1. The reactor is stirred at medium speed and 30 Kg of salicylaldehyde is charged to the reactor. The reaction mixture is then cooled to less than 10° C. The temperature is kept at less than about 20° C. while 7.38 Kg of ethylenediamine is charged to the reactor. The mixture in the reactor is stirred for at least 16 hours at room temperature. The reactor contents are centrifuged then washed with 20 L of EtOH/5% IPA. The material is collected and dried in a Stokes oven at 70° C.±5° C. with at least 26" vacuum for at least 16 hours. This provides the product indicated in Reaction Sequence I as formula (1).

2. 274 L of THF is charged into a clean 100 gal reactor. The reactor stirring mechanism is started at a medium speed. 113 L of a mixture of EtOH with 5% IPA, along with 34 Kg of the product of Part 1 of this example is charged to the reactor. The reactor is then purged with nitrogen and nitrogen bleed is used throughout the following process. The reaction mixture is cooled to less than 10° C. and 10.110 Kg of sodium borohydride is charged to the reactor while keeping the temperature less than 30°. The mixture in the reactor is stirred for at least 12 hours at room temperature and a sample is removed to determine if there is any starting material left in the reactor. Once the reaction is complete, the reactor contents are concentrated in vacuo and the solvent is stripped until 30 gal remain in the reactor. Then the vacuum is released and the reaction mixture is cooled to less than 30° C. 274 L of DCM are then added to the stirring contents of the reactor and half the reaction mixture is transferred to an adjacent reactor. 100 L of deionized water is added to each reactor and the resulting mixture in each reactor is stirred for at least 15 minutes. The stirring is stopped and the layers are allowed to settle for at least 15 minutes. The bottom organic layers are drained into a stainless steel tank and the aqueous layer is drained and discarded. 10 Kg of sodium sulfate is added to the organic layers in the stainless steel tank and the resulting mixture is stirred for at least 15 minutes then allowed to settle for at least 15 minutes. The solid material is filtered on a ceramic funnel and the filtrate is returned to a reactor and washed with 20 L of DCM. The reactor contents are refluxed at atmospheric pressure and the solvent is stripped to one-half the original volume. The mixture is then cooled to less than 25° C. and the material is filtered on a ceramic funnel sending the filtrate to an adjacent reactor A. The solid obtained in the previous step is suspended in 70 L of DCM. The DCM mixture in the reactor is stirred at medium speed for at least 12 hours and the resulting material is filtered on a ceramic funnel and collected for the next step. The filtrate is set aside in a vessel B. The resulting material is shown as Formula (2) in Reaction Sequence I. The filtrate collected previously in reactor A is then mixed with 120 ml of hexane and the resulting mixture is stirred for at least 3 hours. The resulting solid material is filtered on a ceramic funnel and collected for the next step, also as Formula (2). 70 L of hexane is added to the filtrate obtained in vessel B, and the mixture in the reactor is stirred for at least 2 hours, filtered on a ceramic tunnel collected and packaged. This is further material shown as Formula (2) in Reaction Sequence I.

3. 128 L of chloroform is charged into a clean 100 gal reactor. The stirring speed is kept at 60–90 rpm for this step. 16.3 Kg of the product identified as Formula (2) is added to the reactor. The reactor is heated to about 45° C. Keeping the temperature between 45° C. and 50° C., 25.5 Kg of potassium carbonate is added to the reactor. The resulting reaction mixture is cooled to 40–45° C. and 2.65 Kg tetrabutyl ammonium bromide is added. The reaction mixture is cooled to 35–40° C. and stirring is continued. 25.5 Kg of t-butyl bromoacetate is then added to the reactor and the mixture in the reactor is allowed to stir for at least 48 hours at 35–40° C. Samples are removed from the reactor to determine if any starting material remains. Stirring is continued until no more starting material is detected. The reactor contents are centrifuged and washed with 20 L of chloroform. The filtrate is returned along with the wash to a 100 gal reactor. The reactor is then stirred and charged with 60 L of deionized water and stirred for at least 15 minutes. The stirring is stopped, the layers are allowed to separate for at least 15 minutes, and the bottom organic layer is drained into a tank. The aqueous layer is drained into tanks and discarded. Sodium sulfate (3.2 Kg) is then charged to the tank containing the organic layer and stirred for at least 15 minutes and then filtered on a ceramic funnel. The filtrate is send to a reactor which is then heated under vacuum of at least 20" and the solvent is stripped to an oily material keeping the temperature less than about 40° C. The vacuum is released and the reaction mixture is cooled to 20–30° C. 86 L of hexane are added to the stirring contents of the reactor to form solid material that settles out. The reactor contents are centrifuged and washed with about 10 L of hexane. The solid product is collected and dried in a Stokes oven at 60±5° C. with at least a 26" vacuum for at least 16 hours. This provides the di-t-butyl ester shown as Formula (3) in Reaction Sequence I.

4. 25.75 L of formic acid is charged into each of 2 clean 50 L flasks. Moderate stirring is started in the flask and continued while 12.9 Kg of the t-butyl ester of HBED from the previous step is added. Each flask is heated to 40±5° C. and the temperature is kept between 40–45° C. for at least 48 hours with continued stirring. A sample is removed from the reactors to determine if there are any starting materials available. Once there are none, the reaction mixture is cooled to less than 25° C. 245 L of diisopropyl ether is then charged into a 100 gal tank. The diisopropyl ether is stirred and the contents of each 50 L flask is added to the 100 gal tank. The mixture in the tank is stirred for at least 20 minutes then allowed to settle for at least 30 minutes. The solvent layer (the upper layer) is removed and discarded. Next, 86 L of a mixture of EtOH/5% IPA is added to the tank. The mixture is stirred until fully dissolved, then 135 L of diisopropyl ether is added and stirred for at least 30 minutes. After settling, the material is filtered on a ceramic funnel and washed with 20 L of diisopropyl ether. 49 L of a mixture of EtOH and IPA is charged into a 65 gal tank. The material in the 65 gal tank is stirred and the solid from the ceramic funnel is charged into the tank the mixture is stirred until dissolved. 74 L of diisopropyl ether is added to the stirring contents of the 65 gal tank and the resulting solid material is filtered on a ceramic funnel and washed with 10 L of diisopropyl ether. The sample, if more than 94% pure, is collected and dried in a Stokes oven at 60°±5° C. with at least a 26" vacuum for at least 16 hours. This results in HBED shown as Formula (4) in the Reaction Sequence.

5. 10 L of pyrogen-free water (Water For Injection—WFI) is added into a clean pre-rinsed 50 L flask. The contents are stirred at about 80–120 rpm and 3.00 Kg HBED is added to the stirred contents of the flask. A mixture of 309 g of sodium hydroxide and 8.00 L of WFI water is prepared to form a sodium hydroxide solution. Over the course of 1.5 to 2.5 hours the sodium hydroxide solution is charged to the flask keeping the temperature below 25° C. Once a pH range of 7.1 to 7.3 is reached, the mixture in the flask is allowed to stir for at least 15 minutes and water is added until all material goes into solution. The solution is sent through a Whatman PTFE 0.45 micron disposable cartridge filter into a 5 gal glass carboy. The solution is lyophilized using 1.5 L solution per tray. The material is frozen at −20° C., lyophilized at 0° C., and dried at 20° C. Each batch is dried to less than 5% water, as determined by the Karl Fisher technique. This provides HBED as the mono-sodium salt shown in as Formula (5) is the reaction sequence. This material is shown to be a hydrate.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

The subject matter claimed is:

1. A process for forming N,N'-bis(2-hydroxybenzyl)-ethylenediamine-N,N'-diacetic acid (HBED) which process comprises hydrolyzing a compound of formula (3) to form HBED, wherein formula (3) is:

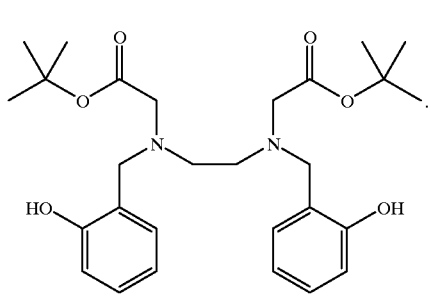

(3)

2. The process of claim 1 wherein the weak acid is formic acid.

3. A process of forming a monocationic salt of N,N'-bis-(2-hydroxybenzyl)-ethylenediamine-N,N'-diacetic acid (HBED), which process comprises reacting one molar equivalent of an organic or inorganic base with HBED.

4. The process of claim 3, wherein the inorganic base is aqueous sodium hydroxide.

* * * * *